United States Patent [19]
Durkan

[11] 3,976,065
[45] Aug. 24, 1976

[54] DIGITAL FLUIDIC VENTILATOR

[76] Inventor: Gerald Durkan, 6 Emerson St., Uniontown, Pa. 15401

[22] Filed: Mar. 10, 1975

[21] Appl. No.: 557,100

[52] U.S. Cl. .............................................. 128/145.8
[51] Int. Cl.² ...................................... A61M 16/00
[58] Field of Search............ 128/145.8, 145.5, 145.6, 128/142, 142.2, 142.3, 2.08, 209, 210, 188, 146.5, DIG. 10, DIG. 17, 147, 349 B, 349 BV; 137/624.13, 624.14, 809, 810

[56] References Cited
UNITED STATES PATENTS

| | | | |
|---|---|---|---|
| 3,435,822 | 4/1969 | Ziermann et al. ............ | 128/DIG. 10 |
| 3,529,596 | 9/1970 | Garner.............................. | 128/145.6 |
| 3,537,449 | 11/1970 | Foxwell et al. ................... | 128/145.5 |
| 3,586,021 | 6/1971 | McGuinness ..................... | 128/145.6 |
| 3,659,598 | 5/1972 | Peters et al. ...................... | 128/145.8 |
| 3,736,949 | 6/1973 | Wolter et al...................... | 128/145.8 |
| 3,756,229 | 9/1973 | Ollivier ............................. | 128/145.8 |
| 3,768,468 | 10/1973 | Cox................................... | 128/145.8 |
| 3,788,326 | 1/1974 | Jacobs.............................. | 128/349 B |
| 3,814,091 | 6/1974 | Henkin ............................. | 128/145.8 |
| 3,840,006 | 10/1974 | Buck et al........................ | 128/145.8 |

OTHER PUBLICATIONS

Ball et al., Fourth Cranfield Fluidics Conference, Mar. 17-20, 1970, Coventry, pp. 13-24.

Belforte, Fourth Cranfield Fluidics Conference, Mar. 17-20, 1970, Coventry, pp. 1-12.

Primary Examiner—Robert W. Michell
Assistant Examiner—Henry J. Recla
Attorney, Agent, or Firm—Griffin, Branigan and Butler

[57] ABSTRACT

A single fluidic flipflop serves as the primary control element in a respiratory ventilator, the flipflop selectively controlling an interface valve to intermittently interrupt the flow of gas from a source to the lungs of a patient through a flow line. In a pressure-limited embodiment positive and negative pressures in the flow line control the flipflop whereas in a volume limited embodiment a negative pressure provides one control for the flipflop and the second control is digitally derived from the volume of gas flowing to the patient. The ventilator is operable in the assist, control and intermittent mandatory ventilation modes. It may operate as an intermittent positive pressure breathing device or a positive end expiratory pressure device, depending upon a manually adjustable bias signal applied to the flipflop. Provision is made for both a manual and an automatic sigh control, and for selectively inflating an endotracheal cuff.

19 Claims, 6 Drawing Figures

DIGITAL FLUIDIC VENTILATOR

BACKGROUND OF THE INVENTION

The use of volume ventilators in clinical medicine is well established and a number of these devices, to one degree or another, employ fluidic control elements. However, many of the known devices are large and cumbersome. Some require electric components, thus creating a safety hazard when used in an operating room where flammable gases are present. Others require relatively large power sources whether they be electrical of fluidic sources. Still others suffer the disadvantage that they must be sterilized after each use.

Warren U.S. Pat. No. 3,292,623 is exemplary of a prior art ventilator employing a fluidic element. However, the patented device has the disadvantage that the "power" is always on and thus much oxygen is wasted. Furthermore, it takes a relatively large negative inspiratory pressure to operate the controlling flipflop since this flipflop is actuated through its output port, and the expiratory impedance is clinically undesirable. Burns U.S. Pat. No. 2,280,832 shows another fluidic ventilator which also has an undesirably high expiratory impedance. Furthermore, contamination of this patented device is inevitable.

More recently, fluidic ventilators have been developed which provide more selectively in the operational mode. Wolter, et al., U.S. Pat. No. 3,736,949 is typical of these devices. However, insofar as is known, no fluidic ventilator has been developed which can operate in the assist, control, or intermittent mandatory ventilation mode, that is provided with sigh control, and can be operated as an intermittent positive pressure breathing device or a positive end expiratory pressure device.

While volume cycled ventilators are known in the art, most of these devices determine tidal volume by calibrating for a certain flow rate and then timing the flow over an interval of time. While this method is satisfactory as long as the flow rate remains constant, if provides an erroneous indication of tidal volume if, for example, the pressure of the source should vary.

SUMMARY OF THE INVENTION

An object of the present invention is to provide a respiratory ventilator selectively operable in many modes and having none of the disadvantages associated with ventilators of the prior art.

An object of the invention is to provide a respiratory ventilator wherein the primary control is obtained by a fluidic flipflop, the primary moving part is a valve operated by the flipflop, and wherein any one of a plurality of operating modes is obtained by adjusting a bias signal applied to the flipflop.

An object of the invention is to provide a respiratory ventilator for controlling the flow of gas to a patient through a flow line, and including a biased fluidic flipflop, a valve in the flow line and actuated by the flipflop for selectively passing or blocking the flow of gas through the flow line, and first and second sensing means each including a fluid diode and connected the flow line to the flipflop whereby negative inspiratory pressures in the flow line set the flipflop and the peak positive inspiratory pressure in the flow line resets the flipflop. The bias means for the flipflop is manually adjustable to select the inspiratory effort required of a patient to initiate a cycle of the ventilator in the assist mode, and is further adjustable to select either the intermittent positive pressure beathing mode or the positive end expiratory pressure mode.

A second embodiment of the invention is similar to that described in the preceding paragraph, except that it is volume limited rather than pressure limited. That is, the volume of gas flow, rather than the peak inspiratory pressure, determines when the flipflop is reset. An analog to digital converter senses the volume of gas flow through the flow line and produces a sequence of output pulse proportional in number to the volume flow. These pulses are counted by a predetermined counter which produces a signal to reset the flipflop each time a volume of gas, as selected by the setting of the counter, has passed through the flow line to the patient.

A feature of the invention applicable either to the pressure-limited or the volume limited embodiment is the provision of a vortex amplifier having an output connected to the flow line and responsive to an air source and an oxygen source for mixing the two in a selected ratio without changing the total volume flow into the flow line. This feature requires separate valves for the two sources, but both valves may be operated from the single fluid flipflop.

Another feather of the invention is the provision of a digital pneumotachometer and counter for determining tidal volume in a respiratory ventilator.

Another feature of the invention is the provision of an automatic sigh control which counts respiration cycles and after each selected number of cycles causes the patient's lungs to be inflated to a higher pressure and for a longer time than a normal cycle.

A further feature of the invention is the provision of a disposable exhalation valve connected to a portion of said flow line which is also removable, the connection of said exhalation valve to the flow line being made at a point whereby the major portions of the ventilator are not contaminated and do not require sterilization, but the contaminated portion of the flow line and the exhalation valve may be disposed of after a single use.

Other objects, features, and advantages of the invention will become obvious upon consideration of the following description and the accompanying drawings wherein like reference numberals have been applied to corresponding elements throughout the several figures.

DESCRIPTION OF THE PREFERRED EMBODIMENTS

Figure 1:
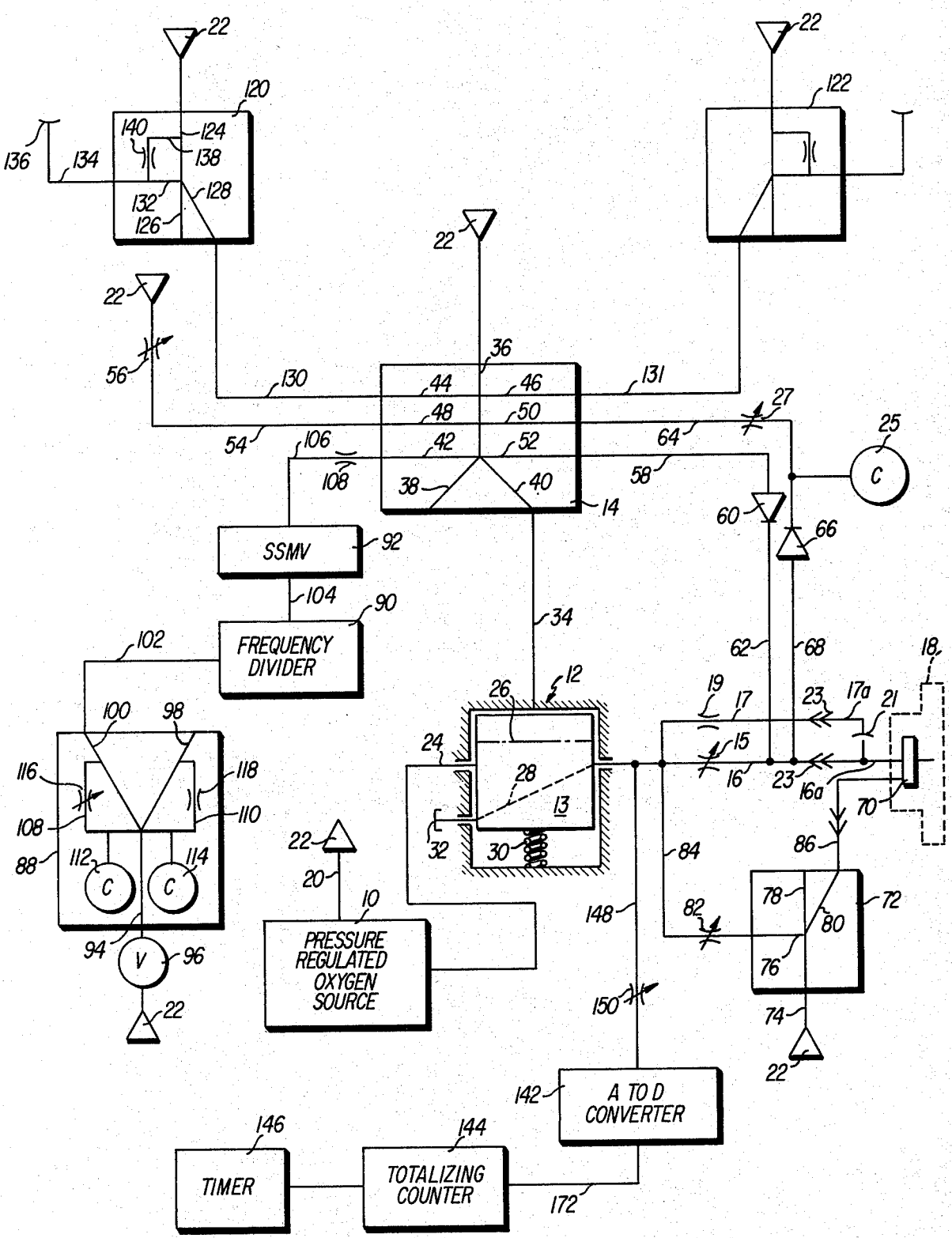
FIG. 1 is a schematic diagram of a pressure-limited respiratory ventilator with a single gas source.

FIG. 1 shows a respirator or ventilator constructed in accordance with the principles of the present invention and including a source of oxygen 10, an interface valve 12, a bistable fluid amplifier or flipflop 14, and fluid conveying means 16 for conveying oxygen from the interface valve into the mouth, throat and lungs 18 of a patient. For purposes of brevity, any fluid conveying means, such as a duct, pipe, channel, or other closed fluid conduit is hereinafter referred to as a line.

The source 10 may comprise a cylinder of compressed oxygen with conventional pressure regulating means whereby oxygen is continuously available at the output of source 10 at a reasonably constant pressure on the order of 30–50 psi. A protion of the oxygen output from source 10 is applied over a line 20 to a manifold connection 22 from whence it is applied to various fluidic control elements hereinafter described. The remaining portion of the oxygen output from source 10 is applied through a line 24 to the interface valve 12.

Interface valve 12 may be of the type available from Bowles Engineering Corp., Catalog No. V-025-A. The valve is a fluid actuated device having two channels 26 and 28 extending through a piston 13 contained within a piston chamber. Normally, a spring 30 biases the piston so that the channel 28 forms a connecting channel between the line 16 and a port 32. However, in the present application the port 32 is plugged. Upon application of a fluid signal over a line 34, piston 13 moves downwardly against the bias of spring 30 so that the channel 26 forms a connecting channel between lines 24 and 16 thereby supplying oxygen to the patient 18. Upon termination of the fluid signal on duct 34, spring 30 returns the piston 13 to its upward position thereby cutting off the flow of oxygen to the patient.

Flipflop 14 is the primary control element for the ventilator and may be a conventional bistable fluid amplifier of a type well known in the art. The flipflop includes a power stream input 36 connected to oxygen source 10 through connector 22, a first output 38 which is vented to the atmosphere, and a second output 40 which is connected by way of line 34 to the chamber of the interface valve 12. In the reset state, the power stream is directed to output 38 whereas for the set state the power stream is directed toward output 40.

Flipflop 14 has six control inputs 42, 44, 46, 48, 50, and 52. The purpose of control inputs 42, 44, 46 is explained subsequently. Control input 48 is connected by a line 54 and the connector 22 to the oxygen source 10 and serves as a bias input to the flipflop. A needle valve or other variable flow restrictor 56 is inserted in the line 54 to provide a means for varying the positive pressure bias signal applied to control input 48. Control input 52 is connected by a line 58, a check valve or fluid diode 60, and a line 62 to the line 16. Control input 50 is connected to line 16 through a line 64, a fluid diode 66, and a line 68.

An exhalation valve 21 is provided through which gas exhaled from the patient's lungs may be vented to the atmosphere. A line 17 is tapped into line 16 intermediate interface valve 12 and a flow restrictor 15. The line 17 contains a pressure reducing flow restrictor 19 and is connectable to the valve 21 through a disconnectable line segment 17a for the purpose of holding the valve closed when valve 12 is open. The line 16 is extended to the patient by a disconnectable line segment 16a. As will be evident from the subsequent description, gas exhaled by a patient never passes from line 16a 16a into line 16, hence the ventilator is never contaminated beyond the connection 23 and does not require sterilization. The line segments 16a and 17a as well as the exhalation valve may be made of sterilizable material and sterilized after each use, or these parts may be made of an inexpensive material and discarded after one use.

The apparatus thus far described is capable of operating as an intermittent positive pressure breathing (IPPB) device in either the assist or the control mode, or as a positive end expiratory pressure (PEEP) device in the control mode. The various modes of operation are selected merely by adjustment of the variable restrictor 56.

Consider first the assist mode where the ventilator assists a patient able to breath on his own. The variable restrictor 56 is set so as to apply a small positive bias signal to control input 48 of flipflop 14, the bias signal being of such small magnitude that it does not cause the flipflop to switch from the reset to the set state. The power stream of the flipflop remains directed toward output 38 until the patient begins to inhale. When the pateint inhales a negative pressure which may be quite small, (i.e. 1 cm of water) is produced on line 16 because exhalation valve 21 closes and the interface valve is isolating line 16 from oxygen source 10. The negative pressure signal on line 16 passes over line 62, through fluid diode 60, and over line 58 to the control input 52 of the flipflop. This negative signal acting on one side of the power stream of the flipflop, in combination with the positive bias signal applied to control input 48 and acting on the other side of the power stream, is sufficient to switch the flipflop from the reset state to the set state. The resulting signal from output 40 is applied over the line 34 to the interface valve 12 where it drives the piston 13 downwardly against the force of spring 30 until such time as the channel 26 in the piston is aligned with lines 24 and 16. As the channel 26 becomes aligned with lines 16 and 24, oxygen from source 10 passes through the interface valve and the line 16 into the patient. Flow restrictor 15 as provided to control the rate of oxygen flow to the patient and prevents too rapid an inflation of the lungs when the 30–50 psi output of source 10 is applied to line 16. At the same time, the line 17 is pressurized by oxygen from the source 10 thereby keeping the exhalation 21 closed.

Oxygen is supplied to the patient over line 16 and the line 17 is pressurized to hold the exhalation valve 21 closed as long as the patient inhales. The pressure on line 16 increases to a range of 15 to 50 cm. of water. This pressure is communicated over line 68, through fluid diode 66, and over line 64 to the control input 50 of the flipflop. The variable restrictor 27 directly controls the peak inspiratory pressure and indirectly the tidal volume. The signal at control input 50 is of sufficient magnitude to overcome the bias signal applied to control input 48 so the flipflop switches back to its reset state. As the flipflop is reset the pressure signal on line 34 is terminated and the return spring 30 returns the piston 13 to the position shown in FIG. 1. This terminates the flow of oxygen through the interface valve to the lines 16 and 17. Termination of the high pressure flow to the exhalation valve 21 allows it to open so that the patient exhales through a low impedance. The flipflop 14 remains reset as long as the patient exhales and it is again set when the patient begins to inhale, thereby initiating another cycle like the one just described.

From the above description it is seen that the inspiratory effort necessary to initiate a cycle of operation is dependent upon the magnitude of the bias signal applied to control input 48 of the flipflop. As the variable restrictor 56 is adjusted to decrease the bias signal at control input 48, more inspiratory effort on the part of the patient is required in order to initiate a cycle of operation. On the other hand, adjustment of the variable restrictor 56 to increase the bias signal causes a decrease in the inspiratory effort required to initiate a cycle. In fact, by further opening the variable restrictor 56 a bias signal is applied to control input 48 which is of such magnitude as to require no inspiratory effort on the part of the patient. The device then operates in the control mode, and this mode is particularly useful in those situations where the patient is unable to breath by himself.

In the control mode just mentioned, the bias signal applied to control input 48 of the flipflop is of a magnitude sufficient to normally switch the flipflop to the set state. The resulting signal on line 34 operates the interface valve 12 so that oxygen from source 10 passes through the valve and over line 16 to the patient. At the same time, the output from the interface valve passes over line 17 to close exhalation valve 21. As oxygen flows through the line 16 into the patient's lungs, the lungs fill and the pressure in line 16 begins to increase. This pressure is communicated over line 68, through diode 66, and over line 64 to the control inputs 50 of the flipflop. Eventually, the pressure in line 16 becomes great enough such that the signal applied to control input 50 overcomes the bias signal applied to control input 48 so the flipflop switches to its reset state. This terminates the signal on line 34 and allows the interface valve to return to the position as shown in FIG. 1. When the interface valve closes, the flow of oxygen through line 16 to the patient is terminated. Furthermore, with interface valve 12 closed, the high pressure flow on line 17 is terminated thereby permitting the exhalation valve 21 to open. The pressurized fluid on line 16 and in the patient's lungs is thus vented to the atmosphere through the exhalation valve. As exhalation takes place, the pressure signal in line 16 is continuously transmitted over lines 68 and 64 to the control input 50. When this signal drops to, or slightly below, the magnitude of the bias signal applied to control input 48, the bias signal again sets the flipflop so that its power stream is directed to the output 40. This initiates another cycle.

A fluid capacitance 25 is connected to line 64 between control 50 and restriction 27 to provide a delay in the signal transmitted over line 64. This insures that the flipflop is not set too soon, and extends the time between the end of one exhalation and the next inhalation.

If the variable restrictor 56 is adjusted so that the bias signal applied to control input 48 is even greater than that just described for the control mode, the end expiratory pressure never reaches zero and the valuable method of positive end expiratory pressure (PEEP) is achieved. This allows a lesser concentration of oxygen to be used in order to achive a higher partial pressure of oxygen in the blood. Some respirators now use a column of water to inhibit flow through the exhalation valve to achieve PEEP pressure. This is sloppy and promotes the growth of dangerous water-growing bacteria that are a menace in IPPB devices. It is well known that oxygen toxicity can occur with high concentrations of oxygen, especially above 40%, flowing into the lungs. With the use of PEEP, adequate oxygen saturation can be achieved at a lower fractional oxygen concentration going into the lungs.

With controlled ventilation and especially the use of PEEP, a cuffed endotracheal tube is necessary. The cuff 70 is a toroidal shaped inflatable device that fits into the patient's trachea and surrounds the tracheal tube 16a through which oxygen is supplied to the lungs. When the cuff 70 is inflated it forms a seal around the tracheal tube and against the tracheal wall so that oxygen supplied to the patient through the tracheal tube 16a cannot escape from the patient's lungs. In the past, such cuffs have been known to cause necrosis of the trachea if too high a pressure is maintained in it. This is most noticeable when cuffed endotracheal intubation is carried out for any length of time. Low pressure-higher volume cuffs have been used to decrease this hazardous condition. However, it has been found that intermittent inflation and deflation of the cuff during the respiratory cycle is even more desirable. This is achieved in the present invention through the use of a fluid NOR circuit 72 having a power stream input 74, a control input 76, and first and second outputs 78 and 80. The power stream input 74 is connected through connection 22 to the pressure regulated oxygen source 10. The control input 76 is connected through a variable restrictor 82 and a line 84 to the line 16, the connection to line 16 being made between the interface valve 12 and the restrictor 15. The output 78 of NOR 72 is vented to the atmosphere and the output 80 is connected by a line 86 to the cuff 70.

As long as interface valve 12 is closed so that no oxygen is applied over line 16 to the patient, there is no flow over line 84 to control input 76 so the power stream of NOR circuit 72 is vented to the atmosphere through output 78. When the interface valve is opened so that oxygen from source 10 is applied over line 16 to the patient, a portion of the flow in line 16 is diverted over line 84 to control input 76 thereby deflecting the power stream of NOR circuit 72 to the output 80. This pressurizes the line 86 and the cuff 70, and the cuff thereby forms a seal in the tracheal tube to prevent the escape of oxygen from the patient's lungs. When the interface valve again closes, the signal on line 84 terminates and the power stream of NOR circuit 72 returns to its initial state and vents to the atmosphere through output 78. This permits cuff 70 to deflate. A negative pressure in output 80 during deflection helps to evacuate the cuff, since aspiration occurs in this channel when flow is directed to output 78.

The ventilator of FIG. 1 is also capable of operating in the intermittent mandatory ventilation (IMV) mode. This mode is useful where the patient may be able to breath either partially or fully on his own, but where it is desirable to insure a respiration rate on the order of less than 10 breaths per minute. An oscillator 88, a frequency divider 90, and a single shot multivibrator 92 are provided for controlling the IMV mode.

Oscillator 88 has a power stream input 94 connected through a cutoff valve 96 and connection 22 to the pressure regulated oxygen source 10. Valve 96 is provided to turn off the power stream of the oscillator and conserve oxygen when the ventilator is not operating in the IMV mode. The oscillator 88 has a first output 98 which is vented to the atmosphere, and a second output 100 connected by a line 102 to the frequency divider 90. The output of the frequency divider is connected by a line 104 to the single shot multivibrator 92 and the output of the multivibrator 92 is connected by a line 106 to the control input 42 of the flipflop 14.

Oscillator 88 is a conventional pure fluid oscillator having feedback paths 108 and 110, fluid capacitances 112 and 114, and flow restrictors 116 and 118. Flow restrictor 116 is variable so as to adjust the rate of oscillation of the oscillator 88 in a manner well known in the art. The oscillator oscillates as long as the valve 96 is open so that a power stream is applied to the oscillator. Output pulses from the oscillator appearing on the line 102 are counted by the frequency divider 90 which may be a conventional pneumatically operated counter that produces a single output pulse on line 104 for each N pulses applied to the counter over the lead 102. Each time the frequency divider 90 produces fluid signal on lead 104, this signal triggers the single shot multivibrator 92 and it produces a fluid pulse of short duration on the line 106.

Flow restrictor 56 is closed when the ventilator is operating the IMV mode so that no bias signal is applied to control input 48 of the flipflop 14. Furthermore, a flow restrictor 108 in the line 106 restricts the magnitude of the output signal from single shot multivibrator 92 to a magnitude insufficient to switch the flipflop if the patient is exhaling so that there is a signal being applied to the flipflop by way of lines 68 and 64 and control input 50. Should the patient be exhaling at the time multivibrator 92 produces a pulse, the frequency divider 90 merely recycles to begin another count and the output pulse from multivibrator 92 has no visible effect on flipflop 14.

If the patient is inhaling at the time single shot multivibrator 92 produces a fluid pulse on line 106, the pulse sets the flipflop 14 so that its power stream is directed toward output 40. The resulting signal on lead 34 operates the interface valve 12 so that oxygen from source 10 passes through the interface valve and over line 16 to the patient. The pressure in line 16 increases to the peak inspiratory pressure at which time the magnitude of the signal transmitted over lines 68 and 64 to control input 50 is of sufficient magnitude to switch the flipflop to its reset state where it remains at least until the next pulse occurs on line 106. The peak inspiratory pressure is reached either by the added volume of oxygen forced into the patient, or by the lung volume being reduced as the patient begins to exhale. When the flipflop is reset the signal on line 34 terminates and the spring 30 returns the interface valve to its inactive position thereby blocking further flow of oxygen to the patient.

It should be noted that by varying the flow restrictor 116 to reduce the rate of oscillation of oscillator 88, the respirator may be operated in the IMV mode at rates ranging as low as 1 or 2 cycles per minute. This is especially useful in "weaning" patients from respirator use.

The respirator of FIG. 1 may also be operated manually. Two NOR circuits 120 and 122 are provided for this purpose. NOR circuit 120 has a power stream input 124, a first output 126 which is vented to the atmosphere, a second output 128 which is connected by a line 130 to the control input 44 of flipflop 14, and a control input 132 connected by a line 134 to a key 136. A line 138 connects the power stream input 124 to the control input 132 through a flow restrictor 140. The power stream input is connected through connector 22 to the oxygen source 10 and the power stream normally exits to the atmosphere through output 126.

A portion of the power stream is diverted into the line 138 to the control input 132 where most of it normally exits through an opening in the key 136. When an operator places a finger on the key 136, it closes the opening and the fluid flowing in line 138 is directed towards the power stream of the NOR circuit thereby deflecting the power stream to the output 128. The signal at output 128 passes over line 130 and enters control input 44 thereby switching flipflop 14 to its set state. As soon as the operator's finger is removed from the key 136, the power stream of NOR 120 switches back to output 126 but the flipflop 14 remains set.

The NOR circuit 122 functions in the same manner as NOR circuit 120, but is connected to control input 46 of the flipflop 14 for the purpose of resetting the flipflop. Preferably, the magnitudes of the signals applied to control inputs 44 and 46 are of much greater magnitude than the signals applied to the other control inputs of the flipflop whereby the operator is able to override any other control signals applied to the flipflop. These manual controls may be used for many purposes, including use as a manual "sigh" control wherein the patient's lungs are filled to a higher pressure, and for a longer time, than is usual.

The respirator of FIG. 1 is capable of accurately measuring tidal volume, or the volume of oxygen supplied to the patient per unit of time. For this purpose, the respirator is provided with an analog to digital converter 142, a totalizing counter 144, and a timer and/or reset means 146.

The analog to digital converter 142 comprises a fluid digital pneumotachometer of the type disclosed in my U.S. Pat. No. 3,714,828, the disclosure of which is incorporated herein by reference. A line 148 connects with the line 16 at a point between interface valve 12 and flow restrictor 15. The line 148 has a variable flow restrictor 150 therein and is connected at its other end to the input of the analog to digital convertor 142.

Figure 2:
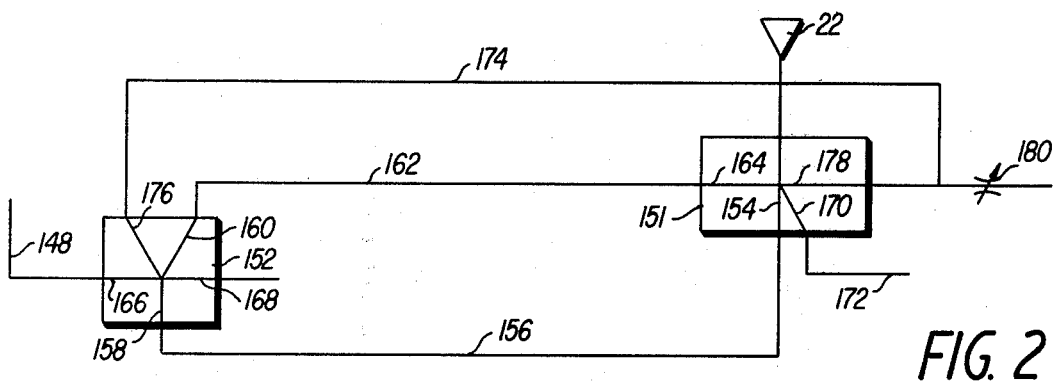
FIG. 2 illustrates an analog to digital converter suitable for use in the present invention.

Referring to FIG. 2, the analog to digital converter 142 comprises a NOR circuit 151 and a proportional fluid amplifier 152. NOR circuit 151 has an output 154 connected by a line 156 to the power stream input 158 of the amplifier 152. Amplifier 152 has an output 160 connected by a lead 162 to a control input 164 of the NOR circuit 151. Amplifier 152 has a first control input 166 connected to the line 148 for receiving a signal whose magnitude provides an indication of the volume of fluid flow through the line 16. The amplifier 152 has a second control input 168 which may either be vented to the atmosphere or connected to a suitable bias source.

NOR circuit 151 has a second output 170 which is connected by a line 172 to the input of the totalizing counter 144. As explained in detail in my aforementioned patent, the power stream of NOR 151 oscillates back and forth between its outputs 154 and 170 at a rate dependent upon the magnitude of the signal applied over lead 148 to the proportional amplifier 152. As NOR circuit 151 oscillates it produces fluid pulses on lead 172 and these pulses are counted by the totalizing counter 144 which may be a low pressure Kessler-Ellis pneumatic counter.

The analog to digital converter may be calibrated by means of the variable restrictor 150. By opening restrictor 150, the converter 142 will produce more output pulses for each unit volume of oxygen passing through line 16.

A line 174 connects an output 176 of proportional amplifier 152 to a second control port 178 of the NOR circuit 151. The line 174 is also vented to the atmosphere through an orifice valve or restrictor 180 which may be adjusted to obtain a null balance in NOR circuit 151. The line 174, which is not shown in my aforementioned patent, is provided for the purpose of obtaining better linearity over a wide range of flows being measured.

The timer mechanism 146 may be any suitable mechanism for enabling the totalizing counter 144 for a predetermined duration of time such as, for example, one minute. Alternatively, the totalizing counter 144 may be provided with a manual reset in which case an operator may reset the counter and then observe the reading on the counter after a predetermined time has elapsed.

In some ventilators of the prior art it has been the practice to insert a venturi in the line 16 for the purpose of diluting the pure oxygen source 10 with air. While this arrangement would be satisfactory for use in the apparatus of FIG. 1 when the ventilator is operated in the control mode, the ventilator would not function properly in the assist mode. The reason for this is that in the assist mode a negative inspiratory pressure could not be obtained in the line 16 if the line contained a venturi open to the atmosphere. It is this negative inspiratory pressure that is used to set the flipflop 14 through control input 52.

Figure 3:
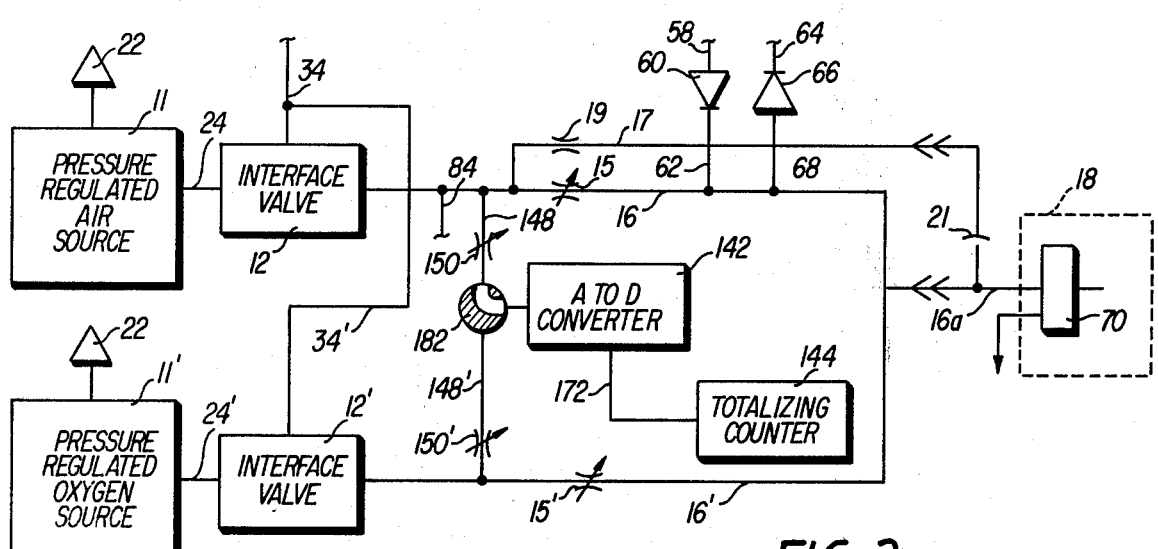
FIG. 3 is a schematic diagram of a pressure-limited respiratory ventilator having an oxygen source and an air source.

The present day trend in hospitals is to provide both an oxygen and an air tap which may be wall outlets. FIG. 3 shows one arrangement suitable for use in the present invention for mixing the air and oxygen. In FIG. 3, oxygen source 11' and air source 11 represent the wall outlets. Generally speaking, the device of FIG. 3 is like that of FIG. 1 but includes a second interface valve 12' and a second line 16' connected in parallel with interface valve 12 and line 16. A line 34' is connected between the output of flipflop 14 (not shown) and the interface valve 12' so that the interface valves 12 and 12' functin in exactly the same manner. Either one or both of the flow restrictors 15 and 15' may be made variable in order to adjust the relative percentages of oxygen and air mixed together and supplied to the patient. Totalizing counter 144 may be used to measure either air flow or oxygen flow. Oxygen flow is sensed in line 16 by means of the line 148 which is connected to one input port of a selector valve 182. The output port of this valve is connected to the input of the analog to digital converter 142. Air flow in line 16' is sensed by means of line 148' which is connected to a second input port of the selector valve 182. Variable flow restrictors 150 and 150' are provided for purposes of calibrating the totalizing counter. In view of the foregoing description of FIGS. 1 and 2, it should be apparent as to the manner in which the converter 142 and the counter 144 measure either the air flow or the oxygen flow depending upon the setting of the selector valve 182.

In FIG. 3 the flow restrictor 15' is made variable in order to vary the amount of oxygen mixed with the air. However, any variation in the rate of oxygen flow causes a corresponding variation in total flow to the patient. Thus, the totalizing counter 144 is capable of indicating only oxygen flow or air flow but not total tidal volume.

Figure 4:
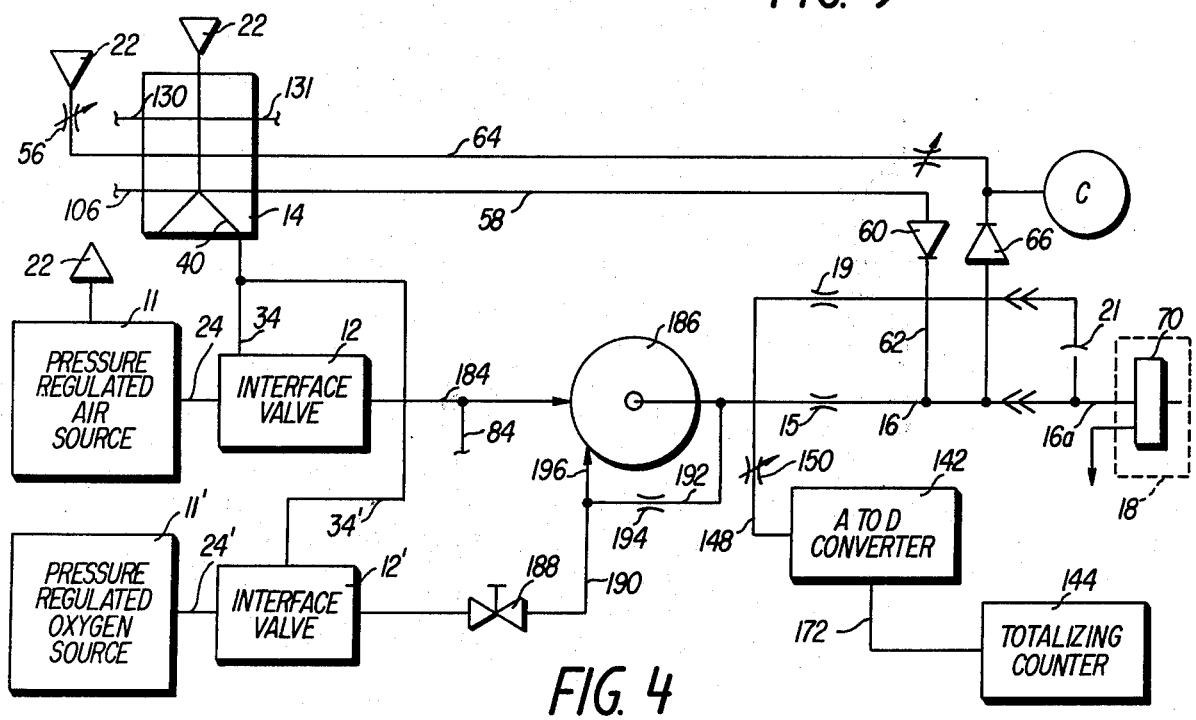
FIG. 4 is a schematic diagram illustrating a pressure-limited respiratory ventilator having an oxygen source, an air source, and a vortex amplifier for mixing the gases from the two sources in different proportions while maintaining a constant total flow.

FIG. 4 shows an arrangement wherein the totalizing counter 144 may indicate tidal volume even though the relative percentages of air and oxygen obtained from two sources may be varied. In this embodiment the pressure regulated air source 11 is connected by line 24 to the input of interface valve 12 and the output of the interface valve is connected by a line 184 to the power input of a vortex amplifier 186. The pressure regulated oxygen source 11' is connected by line 24' to the input of interface valve 12' and the output of interface valve 12' is connected through a flow proportioning valve 188 and a line 190 to the control input of the vortex amplifier. The line 16 extends from the output of the vortex amplifier to the patient 18. The line 190 is connected by a line 192 to the line 16 and the line 192 includes a balancing restrictor 194. The output 40 of flipflop 14 is connected in parallel to interface valves 12 and 12' by means of lines 34 and 34' so that the interface valves act in unison. Except for the elements just described, the embodiment of FIG. 4 may include the same elements and function in the same manner as the embodiment or FIG. 1. However, the embodiment of FIG. 4 provides for mixing the air and oxygen in a predetermined ratio before the mixture is applied to the patient through line 16.

Assume for the moment that the flow proportioning valve 188 is completely closed at the time the flipflop 14 is triggered to its set state. The output of the flipflop, applied over lines 34 and 34' opens both of the interface valves 12 and 12'. However, because the valve 188 is closed there is no flow of oxygen through the line 190. When the interface valve 12 is open, air from source 11 flows through the valve, over line 184, through vortex amplifier 186 and over line 16 to the patient. Thus the patient receives air without any oxygen enrichment.

If the proportioning valve 188 is at least partially open at the time interface valve 12' is actuated, there will be a flow of oxygen from source 11' through interface valve 12', the valve 188, line 190, line 192 and line 16 to the patient. A portion of the flow through valve 188 also enters the control port 196 of the vortex amplifier thereby deflecting at least a portion of the air supplied to the amplifier over line 184 away from the output that is connected to the line 16 so that it is exhausted from the amplifier through another outlet (not shown). As the proportioning valve 188 is opened further, more oxygen will flow over lines 190 and 192 to the line 16 and at the same time a larger magnitude control signal at control port 196 diverts more of the air from the amplifier output connected to the line 16. Thus, by adjusting the valve 188 the operator is able to increase or decrease the degree of oxygen enrichment without changing the total volume of fluid flow through the line 16 to the patient. Furthermore, since the line 148 is connected to the line 16, analog to digital converter 142 produces pulses on the line 176 at a rate dependent upon the actual flow of the air-oxygen mixture to the patient. Therefore, the totalizing counter 144 may provide an accurate indication of tidal volume.

Figure 5:
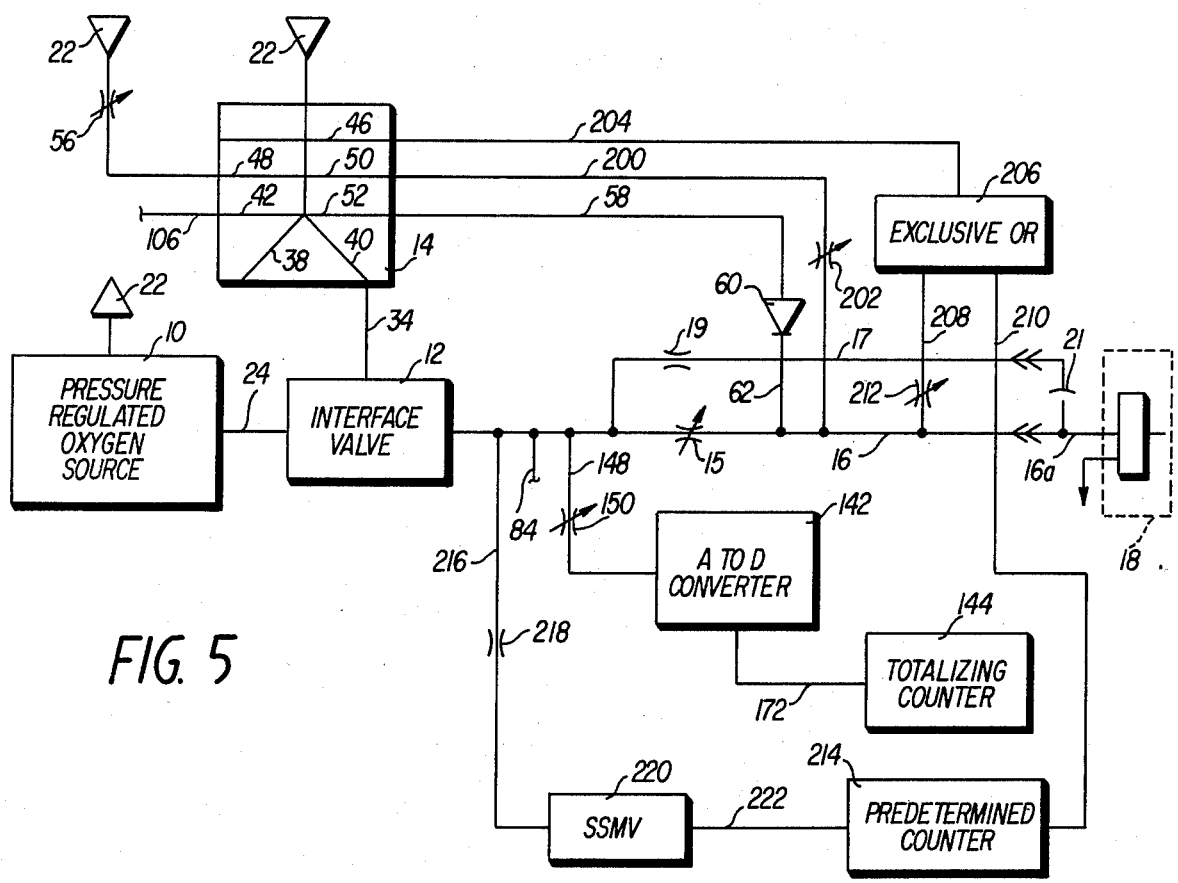
FIG. 5 is a schematic diagram of a pressure-limited respiratory ventilator having an automatic sigh control; and, FIG. 6 is a schematic diagram of a volume limited respiratory controller.

The respiratory ventilator shown in FIG. 5 is quite similar to that of FIG. 1 but differs in that the FIG. 5 embodiment includes means for automatically inducing a sigh after each predetermined number of breaths. The sighs are induced by delaying the reset of the flipflop 14. For this purpose the control input 50 is connected by a line 200 through a flow restrictor 202 to the line 16. The control input 46 is connected by a line 204 to the output of an EXCLUSIVE OR or an INHIBITED OR fluid logic circuit 206. EXCLUSIVE OR 206 has two input lines 208 and 210. Line 208 is connected through a variable flow restrictor 212 to the line 16 and the line 210 is connected to the output of a predetermined counter 214. A line 216 is connected to the line 16 at a point intermediate interface valve and flow restrictor 15, the line 216 being connected through a flow restrictor 218 to the input of a fluidic single shot multivibrator 220. The output of the single shot multivibrator is in turn connected to the input of the predetermined counter 214. The counter 214 is preferably a pneumatically actuated counter having manual control means for determining its counting modulus whereby it produces a fluid output signal on line 210 after every Nth pulse received over the line 222.

The flow restrictors 202 and 212 are adjusted such that it takes a higher pressure on the line 16 to trigger flipflop 14 through restrictor 202 then it does to actuate EXCLUSIVE OR 206 through the restrictor 212. Furthermore, EXCLUSIVE OR 206 produces an output signal on line 204 each time a signal appears on line 208 unless a signal concurrently appears on the line 210 in which case the output of EXCLUSIVE OR 206 is inhibited.

To illustrate the operation of the ventilator, assume that the ventilator is operating in the assist mode and the exhalation portion of the cycle has just been completed. The bias signal at control input 48 in combination with the negative pressure signal applied to control input 52 from line 16 sets the flipflop and the signal on lead 34 activates interface valve 12 so that oxygen from source 10 flows through the valve and line 16 to the patient 18. As the interface valve is opened the pressure in line 16 between the flow restrictor 15 and the interface valve rises rapidly and this signal is transmitted over line 216 to activate single shot multivibrator 220. The multivibrator produces an output pulse that is applied over line 222 to advance the count in counter 214. The flow through line 16 continues and as the patient's lungs are inflated the pressure in line 16 builds up until there appears on line 208 a signal of a magnitude sufficient to produce an output signal from EXCLUSIVE OR 206. The output from the EXCLUSIVE OR is transmitted over line 204 to the flipflop 14 and resets the flipflop.

Assume the counter 214 has been manually set to the value 20. The ventilator goes through 19 cycles like that just described in the preceding paragraph. On the 20th cycle, when the interface valve 12 is opened, the high pressure on line 16 is transmitted by line 216 to the single shot multivibrator 220 and the output of the multivibrator advances the counter 214 to a count of 20 whereby it produces a fluid signal on lead 210 to inhibit operation of the EXCLUSIVE OR circuit 206. Therefore, when the patients lungs are inflated so that the pressure on line 16 reaches the pressure at which the signal on 208 normally activates the EXCLUSIVE OR 206, nothing happens at the output of the EXCLUSIVE OR. The interface valve 12 remains open and the pressure on line 16 rises to a higher value thus inflating the patient's lungs still further. Subsequently, the pressure on line 16 reaches a magnitude such that the signal on line 200 passing through flow restrictor 202 reaches a magnitude sufficient to reset flipflop 14 thereby permitting the interface valve to close. Thus, on every 20th cycle the patient's lungs are inflated for a longer period, and to a higher pressure, thus simulating a sigh.

Figure 6:
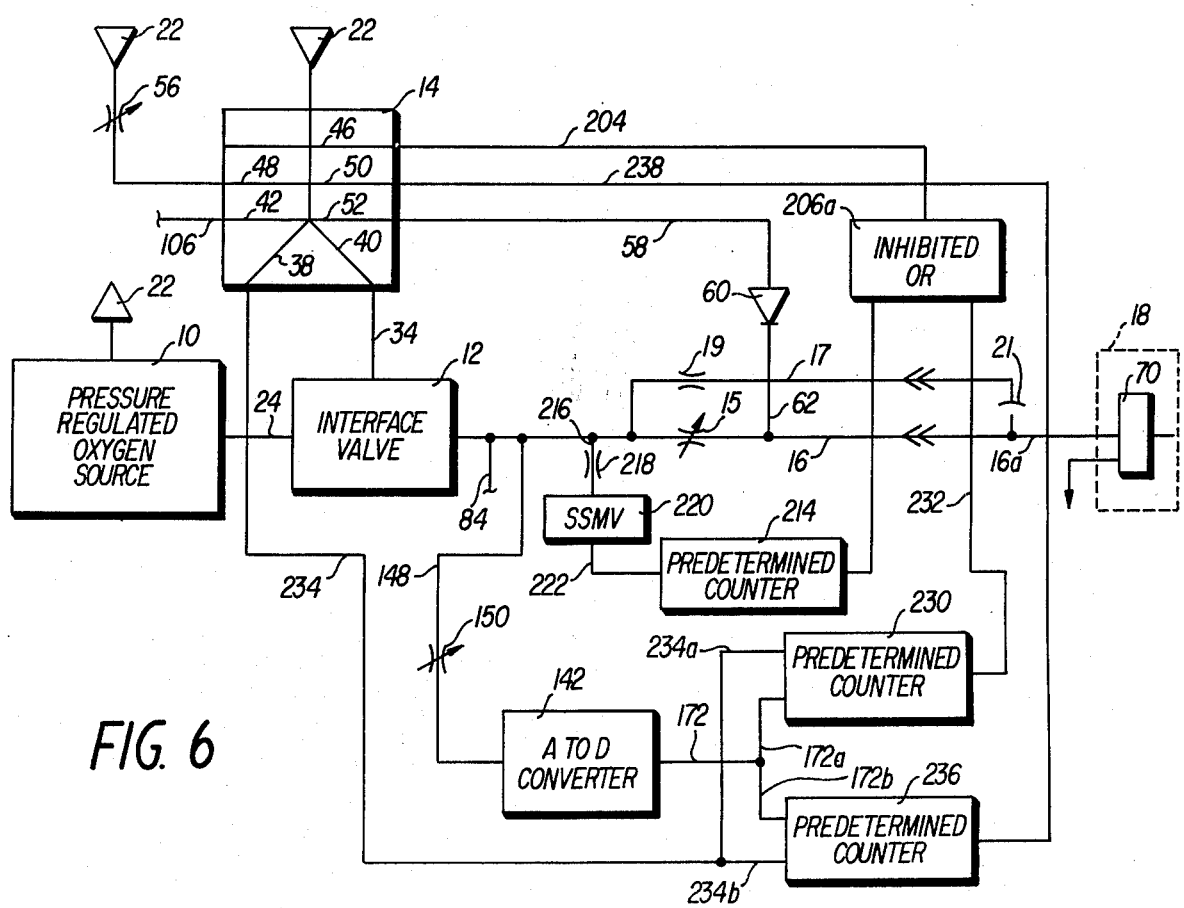

All of the ventilators previously described have been pressure limited. That is, the pressure in line 16 has determined the point at which the flipflop 14 is reset to close the interface valve 12. FIG. 6 shows an embodiment of a volume limited ventilator. That is, on each cycle the flipflop 14 is not reset until a predetermined volume of oxygen has been delivered through the line 16 to the patient.

In the embodiment of FIG. 6 the output of analog to digital converter 142 is connected by lines 172 and 172a to the input of a predetermined counter 230. The output of counter 230 is connected to an input of an INHIBITED OR/NOR circuit 206a by a line 232. For purposes of the present explanation, assume the restrictor 150 is adjusted so that the converter 142 produces one output pulse on the lead 172 for every 10 cc. of oxygen flowing through the line 16. Assume further that the manual control on the predetermined counter 230 is set so that it produces an output signal on the line 232 each time it receives 75 pulses over the line 172a. Thus, for every 750 cc. of oxygen flowing through line 16 the predetermined counter 230 produces an output pulse on the line 232.

Assuming the ventilator is operating in the CONTROL mode and the bias signal applied to control input 48 of the flipflop 14 sets the flipflop, the ventilator operates as follows. The output signal from the flipflop is applied over line 34 to actuate the interface valve 12 whereby oxygen from source 10 flows through the valve and over the line 16 to the patient. A portion of the flow enters lines 148 and is applied to the converter 142 so that the converter produces a sequence of pulses on line 172 representing the volume of flow through the line 16. When 750 cc. of oxygen have flowed through line 16 the converter 142 will have produced 75 pulses on the line 172. These pulses are applied to counter 230 over the line 172a and upon occurrence of the 75th pulse counter 230 produces signal on line 232 to actuate the INHIBITED OR/NOR 206a. The INHIBITED OR/NOR circuit produces an output signal on the lead 204 to reset the flipflop 14 thereby closing the interface valve 12 and terminating the flow of oxygen to the patient.

The reset output 38 of flipflop 14 is connected by a line 234 and a line 234a to a reset input of counter 230. Therefore, when the flipflop is reset the counter 230 is reset thereby terminating the signal on line 232. This in turn deactivates INHIBITED OR/NOR circuit 206a so that the signal on lead 204 is terminated.

The bias signal applied to control input 48 of the flipflop 14 then automatically set the flipflop to begin another cycle for the control mode. Should the ventilator be operating in the assist mode rather than the control mode, then the negative pressure on line 16 when the patient begins to inhale would control the setting of the flipflop 14 in the manner described with reference to FIG. 1, the negative pressure being transmitted to the control input 52 of the flipflop through line 62, fluid diode 60, and line 58.

Predetermined counter 214 in combination with a further predetermined counter 236 operates to provide an automatic sigh control. Counter 214 functions in the same manner as described with reference to FIG. 5 to produce an output signal on lead 210 to inhibit the INHIBITED OR/NOR circuit 206a on every Nth (20th) cycle. The input of counter 236 is connected to the output of analog to digital converter 142 by means of line 172 and 172b so that the counter 236 counts pulses from the converter in the same manner as the counter 230. However, the counter 236 is manually set so that it produces an output signal only after a predetermined number of pulses M, M being greater than N. For purposes of illustration assume that counter 236 produces an output signal for every 90 input signals received from converter 142, or for every 900 cc. of oxygen flowing through the line 16. Output pulses from counter 236 are conveyed to the control input 50 of flipflop 14 by line 238. Counter 236 has a reset input connected by lines 234b and 234 to the reset output 38 of the flipflop 14 so counter 236 is reset each time the counter 230 is reset.

For the assumed values of the settings of the counters 214, 230 and 236, the sigh is produced as follows. On each of 19 consecutive cycles the interface valve opens and oxygen is fed to the patient through the valve in line 16. The analog to digital converter measures the volume flow and produces output pulses to advance both counters 230 and 236. Upon occurrence of the 75th pulse the counter 230 produces an output signal to activate INHIBITED OR/NOR 206a and a signal is produced on lead 204 to reset flipflop 14. When the flipflop is reset the signal on line 234 resets both of the counters 230 and 236.

On each of the 19 cycles the counter 14 is advanced by a count of one when the interface valve 12 is opened and the pressure on line 16 rises. When the interface valve 12 is opened on the 20th cycle to supply oxygen to the patient, the counter 214 is advanced to a counter of 20 and it produces a fluid signal on line 210 to inhibit the operation of INHIBITED OR/NOR circuit 206a. The analog to digital converter 142 measures the flow as in the preceding cycles and upon occurrence of the 75th output pulse from the converter the counter 230 produces an output signal on the lead 232 to the INHIBITED OR/NOR circuit 206a. However, because of the presence of the inhibiting signal on line 210 the INHIBITED OR/NOR circuit 206a produces no signal on the lead 204. Oxygen continues flowing to the patient until the 90th pulse is produced by analog to digital counter 142. This pulse advances counter 236 to a counter of 90 and the counter produces a signal on lead 238 to reset the flipflop 14. When the flipflop is reset the signal on lead 234 resets both of the counters 230 and 236. Therefore, for the assumed conditions, the ventilator of FIG. 6 normally supplies 750 cc of oxygen to the patient, but on every 20th cycle, inserts a sigh during which 900 cc of oxygen are supplied to the patient.

While certain preferred embodiments have been described in specific detail, it should be understood that the drawings have been simplified to better illustrate the various aspects of the invention and various modifications and substitutions may be made in the illustrated embodiments without departing from the spirit and scope of the invention as defined by the appended claim. For example, the air-oxygen mixing and/or proportioning means of FIG. 4 may be incorporated in the embodiments of FIGS. 5 and 6. Furthermore, various gauges and pressure relief valves, not essential to the invention, have not been shown in the drawings. In this regard, it should be noted that the line 16 should be provided with a pressure relief valve so that if malfunction should occur, excessive pressure would not be applied to the patient's lungs. Other modifications and substitutions falling within the spirit and scope of the invention as defined by the appended claims will be evident to those skilled in the art.

I claim:

1. A respiratory ventilator comprising:
   source means providing gas to be administered to a patient's lungs;
   valve means connected to said source means and normally preventing the flow of gas to the patient;
   fluid conveying means for conveying gas from said valve means to the patient when said valve means is activated;
   exhalation valve means connected to said fluid conveying means for exhausting gas exhaled from the patient;
   a fluid flipflop having a set state and a reset state;
   means connecting said flipflop to said valve means to actuate said valve means when said flipflop is in said set state;
   bias means for applying a continuous bias signal of fixed magnitude to said flipflop tending to switch it to said set state;
   first means connected to said fluid conveying means and said flipflop for transmitting a negative inspiratory pressure in said fluid conveying means to said flipflop if the patient begins to inhale, said negative pressure tending to aid said bias signal in switching said flipflop to said set state; and,
   second means connected to said fluid conveying means and said fluid flipflop for transmitting the positive pressure in said fluid conveying means to said flipflop to switch it to said reset state when a predetermined positive pressure is present in said fluid conveying means.

2. A respiratory ventilator as claimed in claim 1 wherein said bias means is manually variable.

3. A respiratory ventilator as claimed in claim 1 wherein said bias means is manually variable to vary the magnitude of said bias signal, whereby the negative inspiratory pressure necessary to switch said flipflop to the set state is varied.

4. A respiratory ventilator as claimed in claim 3 wherein said bias means is manually variable to vary the magnitude of said bias signal to a magnitude sufficient to switch said flipflop to said set state without any negative inspiratory pressure whereby said ventilator operates in the control mode.

5. A respiratory ventilator as claimed in claim 4 wherein said bias means may be varied to a point whereby said bias signal switches said flipflop to the set state and opposes said positive pressure whereby said ventilator operates in the control mode with positive expiratory end pressure.

6. A respiratory ventilator as claimed in claim 1, wherein said source means comprises an oxygen source and an air source, and said valve means comprises a first valve connected to said air source and a second valve connected to said oxygen source;
   said ventilator further comprising means for mixing said oxygen and air in a desired mix, including:
   a vortex amplifier having a power input connected to said first valve, a control input responsive to the output from said second valve, and an output connected to said fluid conveying means;
   a flow proportioning valve connected between said control input and the output of said second valve; and, a fluid conduit means at one end joining said fluid conveying means and at the other end connecting with said control input and said flow proportioning valve.

7. A respiratory ventilator as claimed in claim 1 wherein a variable flow restrictor is provided in said fluid conveying means to permit adjustment of the rate of gas flow to the patient.

8. A respiratory ventilator as claimed in claim 7 wherein said exhalation valve means includes an exhalation valve, means connected to said fluid conveying means upstream of said variable flow restrictor for sensing the pressure thereat for holding the exhalation valve closed, and means connected to said fluid conveying means and the exhalation valve for venting gas from the patient to the atmosphere when the exhalation valve is not closed.

9. A respiratory ventilator as claimed in claim 1 and further including an analog to digital converter responsive to fluid flow through said fluid conveying means for producing fluid pulses proportional to the volume of gas passing through said fluid conveying means;
and a counter for counting said pulses to produce an indication of tidal volume.

10. A respiratory ventilator as claimed in claim 1 further including manually operated switch means for selectively setting and resetting said flipflop whereby manually controlled sighs may be induced.

11. A respiratory ventilator as claimed in claim 1 and further comprising an intermittent mandatory ventilation control for periodically setting said flipflop to initiate inhalation if the patent is not exhaling.

12. A respiratory ventilator as claimed in claim 11 wherein said intermittent mandatory ventilation control comprises an oscillator, a frequency divider, and means responsive to the frequency divider for periodically applying a control signal to said flipflop, said control signal being of a magnitude sufficient to set said flipflop, unless said flipflop is receiving a positive pressure signal of a predetermined magnitude from said second means.

13. A respiratory ventilator as claimed in claim 1 wherein said first means comprises a fluid diode and said second means comprises a fluid diode connected in series with a flow restrictor.

14. A respiratory ventilator as claimed in claim 1 wherein said first means comprises a fluid diode and said second means comprises a fluid logic element connected to said fluid conveying means through a first flow restrictor and responding to a predetermined pressure in said fluid conveying means for producing a signal at the output of said logic element and means for connecting the output of said fluid logic element to said flipflop.

15. A respiratory ventilator as claimed in claim 14 and further including automatic sigh control means, said sigh control means comprising:
means for producing a count pulse each time said flipflop is set;
a counter for counting said pulses and producing an output signal after reaching a predetermined count;
means applying said output signal to said logic element to inhibit any output therefrom in response to said predetermined pressure; and,
means connected between said fluid conveying means and said flipflop for resetting said flipflop when a second predetermined pressure higher than said predetermined pressure is reached in said fluid conveying means.

16. A respiratory ventilator comprising:
source means providing gas to be administered to a patient's lungs;
valve means connected to said source means and normally preventing the flow of gas to the patient;
fluid conveying means for conveying gas from said valve means to the patient when said valve means is activated;
exhalation valve means connected to said fluid conveying means for exhausting gas exhaled from the patient;
a fluid flipflop having a set state and a reset state;
means connecting said flipflop to said valve means to actuate said valve means when said flipflop is in said set state;
bias means for applying a continuous bias signal of fixed magnitude to said flipflop tending to switch it to said set state;
first means connected to said fluid conveying means and said flipflop for transmitting a negative inspiratory pressure from said fluid conveying means to said flipflop when the patient begins to inhale, said negative pressure tending to aid said bias signal in switching said flipflop to said set state; and,
second means connected to said fluid conveying means and said fluid flipflop for applying a signal to said flipflop switch it to its reset state after a predetermined volume of gas has flowed through said fluid conveying means.

17. A respiratory ventilator as claimed in claim 16 wherein said second means comprises:
analog to digital converter means for sensing the flow of gas through said fluid conveying means and producing a sequence of pulses proportional to the volume flow of said gas;
a first counter for counting said pulses and producing an output signal upon reaching a first predetermined count;
means responsive to said output signal for switching said flipflop to said reset state; and,
means connected between said flipflop and said first counter for resetting said first counter.

18. A respiratory ventilator as claimed in claim 17 wherein the means for switching said flipflop to the reset state comprises a fluid logic element having a control input responsive to said first counter and an output connected to said flipflop.

19. A respiratory ventilator as claimed in claim 18 and further including sigh control means, said sigh control means comprising:
a second counter for counting said pulses and producing a reset signal upon reaching a second predetermined count larger than said first predetermined count;
means for applying said reset signal to said flipflop;
means for counting the number of times said flipflop is set and producing an inhibit signal upon reaching a further predetermined count; and,
means for applying said inhibit signal to said logic circuit means to inhibit any output therefrom to said flipflop.

* * * * *